United States Patent
Schiltz

(10) Patent No.: US 7,425,323 B2
(45) Date of Patent: Sep. 16, 2008

(54) TREATMENT AND COMPOSITION FOR ACHIEVING SKIN ANTI-AGING BENEFITS BY CORNEUM PROTEASE ACTIVATION

(75) Inventor: John R. Schiltz, Fairview, TX (US)

(73) Assignee: Mary Kay, Inc., Dallas, TX (US)

( * ) Notice: Subject to any disclaimer, the term of this patent is extended or adjusted under 35 U.S.C. 154(b) by 0 days.

(21) Appl. No.: 11/624,840

(22) Filed: Jan. 19, 2007

(65) Prior Publication Data

US 2007/0196314 A1  Aug. 23, 2007

Related U.S. Application Data

(60) Continuation of application No. 10/273,649, filed on Dec. 12, 2002, now Pat. No. 7,175,837, which is a division of application No. 09/357,288, filed on Jul. 20, 1999, now Pat. No. 6,495,126.

(51) Int. Cl.
*A61K 31/785* (2006.01)
(52) U.S. Cl. .................. 424/78.03; 424/400; 424/401; 424/78.02
(58) Field of Classification Search .......... 424/400, 424/401, 78.02, 78.03; 514/836, 844, 845, 514/846, 847; 510/130
See application file for complete search history.

(56) References Cited

U.S. PATENT DOCUMENTS

| | | | |
|---|---|---|---|
| 4,518,517 A | 5/1985 | Elgen et al. | 252/107 |
| 5,607,678 A | 3/1997 | Moore et al. | 424/401 |
| 5,643,600 A | 7/1997 | Mathur | 424/450 |
| 5,653,970 A | 8/1997 | Vermeer | 424/70.24 |
| 5,720,963 A | 2/1998 | Smith | 424/401 |
| 5,945,093 A | 8/1999 | Duval | 424/70.12 |
| 6,086,903 A | 7/2000 | Trinh et al. | 424/401 |
| 6,184,247 B1 | 2/2001 | Schneider | 514/474 |
| 6,495,126 B1 * | 12/2002 | Schiltz | 424/78.02 |
| 7,175,837 B2 * | 2/2007 | Schiltz | 424/78.02 |
| 7,226,583 B2 * | 6/2007 | Shepherd, Jr. | 424/62 |

FOREIGN PATENT DOCUMENTS

| | | |
|---|---|---|
| WO | WO 97/40816 | 11/1997 |
| WO | WO 97/40817 | 11/1997 |

OTHER PUBLICATIONS

Egelrud and Lundström, "The dependence of detergent-induced cell dissociation in non-palmo-plantar stratum corneum on endogenous proteolysis," *J. Invest. Dermatol.*, 95:456-459, 1990.

Lundström and Egelrud, "Cell shedding from human plantar skin in vitro: evidence of its dependence on endogenous proteolysis," *J. Invest. Dermatol.*, 91:340-343, 1988.

Lundström and Egelrud, "Stratum corneum chymotryptic enzyme: a proteinase which may be generally present in the stratum corneum and with a possible involvement in desquamation," *Acta Der Venereol*, 71:471-474, 1991.

Schiltz et al., "Retinoic acid induces cyclic changes in epidermal thickness and dermal collagen and glycosaminoglycan biosynthesis rates," *J. Invest. Dermatol.*, 87:663-667, 1986.

* cited by examiner

*Primary Examiner*—D. L Jones
(74) *Attorney, Agent, or Firm*—Fulbright & Jaworski LLP

(57) ABSTRACT

Novel methods and compositions for treating aged and environmentally damaged skin are disclosed which provide improvements in the skin's visual appearance, function and clinical/biophysical properties by activating at least one proteolytic enzyme in the skin's stratum corneum. The disclosed treatment methods involve topical application of a novel cosmetic composition containing a combination of a cationic surfactant such as N,N,-dimethyldodecyl amine oxide (DMDAO), an anionic surfactant such as sodium dodecyl sulfate (SDS), or monoalkyl phosphate (MAP) and a chelating agent such as ethylene diamine tetraacetate (EDTA) to stimulate a chronic increase in the replacement rate of the skin's stratum corneum by means of corneum protease activation. This chronic, low level stimulation is effective to induce repair and replacement of the stratum corneum, epidermis, and dermis of the skin and improvements in the appearance, function, and anti-aging properties of the skin.

21 Claims, No Drawings

TREATMENT AND COMPOSITION FOR ACHIEVING SKIN ANTI-AGING BENEFITS BY CORNEUM PROTEASE ACTIVATION

CROSS-REFERENCE TO RELATED APPLICATIONS

This application is a continuation of application Ser. No. 10/273,649, filed Dec. 12, 2002, which is a divisional of application Ser. No. 09/357,288, filed Jul. 20, 1999 (now issued as U.S. Pat. No. 6,495,126), which are incorporated by reference.

FIELD OF THE INVENTION

The present invention relates generally to a treatment method and composition for improving the skin's visual appearance, function, and clinical/biophysical properties which have been changed by factors such as chronological age, chronic sun exposure, adverse environmental pollutants, household chemicals, disease pathologies, smoking, and malnutrition. In particular, the present invention relates to a method of treating skin by increasing the skin's stratum corneum turnover rate through corneum protease activation. More particularly, the invention relates to the use of a combination of a cationic surfactant such as N,N,-dimethyldodecyl amine oxide (DMDAO), an anionic surfactant such as sodium dodecyl sulfate (SDS), and a chelating agent such as ethylene diamine tetraacetate (EDTA) as additives to topically-applied cosmetic skincare products to treat and reduce the clinical and functional signs of aging and environmental damage in skin. The invention provides for an effective alternative to the use of hydroxy acids and retinoid compounds to treat aged and environmentally-damaged skin.

BACKGROUND OF THE INVENTION

With chronological age and chronic exposure to adverse environmental factors, the visual appearance, physical properties, and physiological functions of skin change in ways that are considered cosmetically undesirable. The most notable and obvious changes include the development of fine lines and wrinkles, loss of elasticity, increased sagging, loss of firmness, loss of color evenness (tone), coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, and a reduction in the skin's ability to remodel and repair itself. Many of the above alterations in appearance and function are caused by changes in the outer epidermal layer of the skin, while others are caused by changes in the lower dermis. Regardless of the stimulus for skin damage, when damage occurs, numerous natural and complex biochemical mechanisms are set into motion in attempts to repair the damage.

When the epidermis is injured, the epidermal basal cells respond to the injury by dividing at a more frequent rate. This increase in replication rate results in a more rapid replacement of the damaged epidermis with a new epidermis and stratum corneum, a process referred to as "epidermal cell renewal." Common examples of injuries which can increase epidermal cell renewal rates include abrasion, chemical damage, pH extremes, excessive sun exposure, or allergic or non-allergic contact irritation. If the injury is too severe, the increased replication will result in a "hyperplastic" epidermis and a thickened, poorly-functioning stratum corneum which is manifested as dry, rough scales. Other common stimuli which induce epidermal cell renewal include physical removal of the stratum corneum (i.e., an example of which is tape stripping, a process where tape is applied to the skin and pulled off, removing the top layer of the stratum corneum with it) and friction (i.e., on the soles and heels of the feet), all processes which result in epidermal hyperplasia. Hydroxy acids and retinoids also induce epidermal hyperplasia at appropriate concentrations, although the mechanisms appear to be different. It is believed by many that hydroxy acids exert their effects by inducing physical exfoliation of the corneum, whereas the retinoids more likely work by interacting with cytoplasmic and nuclear binding receptors to alter gene expression. Schiltz, J. et al. "Retinoic acid induces cyclic changes in epidermal thickness and dermal collagen and glycosaminoglycan biosynthesis rates," J. Invest. Dermatol. 87:663-667 (1986), describe various effects of retinoic acid on epidermal and dermal biology including cyclical epidermal thickening and hyperplasia, and dermal changes in the rates of biosynthesis of collagen and glycosaminoglycans.

With chronological age and chronic environmental exposure (notably UVA, UVB, and IR radiation), the dermis undergoes changes in structure and function which result in many of the characteristics of aged skin, including loss of elasticity, formation of wrinkles, loss of water-holding capacity, sagging, and poor microcirculation. At the molecular level, these changes have been correlated with biochemical changes in the content and structure of the extracellular matrix to which the major cells of the dermis (i.e., the fibroblasts) reside. Collagen becomes highly cross-linked and inelastic, elastin is reduced in amounts and is incorrectly distributed, and the glycosaminoglycans become reduced in amounts, which results in reduced intercellular water.

As a result of this changed architecture, the normal amounts and distribution of trace metal ions, growth factors, hormones, and cytokines becomes altered which causes the fibroblasts to become metabolically less active or quiescent. Although these cells have natural mechanisms to repair themselves and the matrix in which they reside, with age and too much damage, they are less able to repair the damage, and the condition continues to deteriorate. If the quiescent fibroblasts can be metabolically activated and stimulated to divide, they will synthesize new extracellular matrix and the old, damaged matrix will be enzymatically degraded and replaced. This process of balanced synthesis and degradation is referred to as "dermal remodeling." The activation process can be accomplished in many different ways, including chemical stimulation by selected hormones, growth factors, cytokines, vitamins, botanical extracts and retinoids, or by increasing the nutrient supply (i.e., blood flow) to the tissue.

Although the mechanisms are not completely understood, it appears that physical or chemical changes to the intact stratum corneum of the skin will result in epidermal basal cell replication and subsequent increases in epidermal cell renewal. If the injury stimulus is too great, the skin will be unable to correct the damage or will "over-respond" in such a way as to cause extensive epidermal hyperplasia and dry, flaky, poorly-differentiated stratum corneum. If the damage stimulus is less and is well controlled, the process of epidermal replacement should result in a healthier, better-functioning epidermis and in a stratum corneum which looks and feels better, has greater capacity to hold moisture, and has fewer surface fine lines.

It is known that damage to the stratum corneum not only sets into motion natural biochemical mechanisms to repair and replace the epidermis, but disturbances in the corneum also stimulate repair and remodeling of the dermis. U.S. Pat. No. 5,720,963 to Smith ("the '963 patent") teaches that chronic and significant disruption of the skin's water barrier using a combination of cerebrosides, hydroxy acids, and retinoids causes chronic injury to the corneum and results in epidermal and dermal repair of the structurally-deteriorated skin if the disruption is maintained for a sufficient period of time. The mechanisms by which the combination of materials used in the '963 patent cause increased epidermal cell renewal and chronic skin repair are entirely different from those which are involved in the current invention. Although the end benefits to the skin are similar, the '963 patent teaches that water barrier disruption agents such as cerebrosides or organic solvents or detergents, in combination with retinoids or hydroxy acids will disrupt the corneum water barrier and stimulate basal cell replication rates. The Applicant has discovered that chronic stimulation of the normal process of desquamation by activation of at least one endogenous corneum protease will result in increased epidermal turnover and epidermal and dermal remodeling. This is not a chronic injury; instead, it is an increase in the rates of corneum shedding by one of the natural mechanisms; the increased desquamation stimulates the natural mechanisms involved in replacing the lost corneum, a process which results in beneficial skin remodeling.

In a series of peer-reviewed scientific publications, Lundstrom, A. and Egelrud, T. "Cell Shedding from Human Plantar Skin In Vitro: Evidence of its Dependence on Endogenous Proteolysis," J. Invest. Dermatol. 91:340-343 (1988); Egelrud, T. and Lundstrom, A., "The Dependence of Detergent-Induced Cell Dissociation in Non-Palmo-Plantar Stratum Corneum on Endogenous Proteolysis," J. Invest. Dermatol. 95: 456-459 (1990); Lundstrom, A. and Egelrud, T. "Stratum Corneum Chymotryptic Enzyme: A Proteinase which may be Generally Present in the Stratum Corneum and with a Possible Involvement in Desquamation," Acta Dermato-Venereol 71:471-474 (1991); investigators from the Department of Dermatology, University Hospital, Umea, Sweden, demonstrated that human stratum corneum possesses endogenous chymotryptic proteinase enzyme(s) which can be activated in vitro by a combination of the cationic surfactant N,N,-dimethyldodecyl amine oxide (DMDAO), the anionic surfactant sodium dodecyl sulfate (SDS), and the chelating agent ethylene diamine tetraacetate (EDTA). Activation of these enzymes resulted in the separation of individual corneum cells (i.e. corneocytes), a process which Egelrud's group has proposed mimics the natural desquamation process. The Egelrud group have described the role of the endogenous chymotryptic proteinase enzyme(s) to be important in natural desquamation of the skin, but their work did not predict that stratum corneum protease activation would enhance the rates of epidermal cell renewal and set up natural epidermal and dermal biochemical mechanisms which could provide benefit to aged or environmentally-damaged skin.

Prior art physiological, chemical, or mechanical methods of increasing stratum corneum renewal rates to achieve benefit such as hydroxy acids, retinoids, barrier disrupters, tape stripping, solvent extraction, etc. all have various drawbacks, such as significant irritation to the skin, skin toxicity, the requirement of high concentrations of expensive ingredients, or of low pH. In addition, all these methods involve the invocation of damage to the skin, which sets up repair mechanisms. For most of these treatments, there will be a period of time, up to several weeks or months, during which the skin becomes irritated and after which tolerance sets in and the symptoms of irritation may decrease and/or cease. When using the method described in the present invention, these drawbacks are not encountered.

Applicant has surprisingly discovered a method of treatment and composition for aged and environmentally damaged skin that enhances the stratum corneum turnover rate by activation of at least one endogenous proteinase. The treatment, which results in skin with improved visual appearance, function, and clinical/biophysical properties, is not known in the prior art. Moreover, the novel method of treatment and compositions of the present invention accomplish this at low concentrations, at a neutral pH, in all the vehicles in which the actives have been tested, and without causing clinical irritation or chronic damage to the skin.

SUMMARY OF THE INVENTION

The features of the invention may be realized and attained by means of the instrumentalities and combinations particularly pointed out in the appended claims. Further features of the invention will be set forth in part in the description which follows and in part will be apparent from the description, or may be learned by practice of the invention.

In accordance with the purpose of the invention in one of its aspects embodied and broadly described herein, there is disclosed a method of treating skin comprising topical application to aged or damaged skin of a cosmetic composition comprising a chemically compatible combination of one or more surfactants and at least one chelating agent, in an amount effective to provide chronic stimulation of the skin's stratum corneum turnover rate, and a reduction in the stratum corneum turnover time, by activating one or more of the skin's endogenous corneum protease enzymes. In another aspect, the present invention includes a cosmetic treatment composition for aged or damaged skin comprising a chemically compatible combination of one or more surfactants and at least one chelating agent, in an amount effective to provide chronic stimulation of the skin's stratum corneum turnover rate, and a reduction in the stratum corneum turnover time, by activating one or more of the skin's endogenous corneum protease enzymes.

Additional aspects of the invention will be set forth in part in the description which follows, and in part will be apparent from the description, or may be learned by practice of the invention. The purposes and features of the invention will be realized and attained by means of the elements and combinations particularly pointed out in the appended claims.

DETAILED DESCRIPTION

The present invention provides a novel method of treatment and a novel composition for treating aged and environmentally damaged or deteriorated skin. The present invention provides a method of treating skin comprising topical application to damaged skin of a cosmetic composition in an amount effective to provide a chronic, increased replacement rate of the skin's stratum corneum by means of corneum protease activation, wherein the increased replacement rate is effective to induce repair, replacement, and remodeling of the stratum corneum, epidermis, and dermis of the skin and improvements in the appearance, function, and aging properties of the skin.

According to the present invention, "increased replacement rate" and "stimulation of the skin's stratum corneum turnover rate" includes any rate of stratum corneum or epidermal turnover which is greater than that of the untreated skin on the same site of the same individual. Typically, this increase in turnover rate, or reduction in turnover time, can range from about 1% to about 40%. Preferably turnover rate is increased by about 25%. There are many different ways in which epidermis and stratum corneum turnover rate can be measured, including but not restricted to assays to measure dansyl chloride disappearance, dihydroxy acetone staining disappearance, or use of radioactive thymidine to measure basal cell labeling index. Chronic stimulation of the stratum corneum turnover rate refers to the repeated, or constant stimulation occurring with regular treatment of the skin with the composition of the present invention.

Similarly, "reduction in skin's stratum corneum turnover time" is the resulting decrease in the time needed for the shedding of the skin layer. The turnover time reduction can range from about 1% to about 40%, preferably the time reduction is about 25%.

"Corneum protease activation" refers to a stimulation, above that of untreated skin, of one or more of the endogenous stratum corneum chymotryptic protease enzymes believed to be involved in the natural desquamation process of corneocyte shedding and subsequent stratum corneum turnover.

The effectiveness of the method of the present invention in providing skin anti-aging benefits can be measured by a number of ways. Each of these strategies for evaluating the effectiveness of the invention can be used independently or together by one skilled in the art. The method is effective when it decreases stratum corneum turnover time by from about 1% to about 40%, preferably by at least about 25%. It is also effective when it reduces TEWL by from about 0% to about 100%, preferably by at least about 1%. It is further effective when it decreases canthus skin roughness by from about 1% to about 60%, preferably by at least about 9%. The method is effective when it decreases the number of wrinkles on the canthus by from about 1% to about 60%, preferably by at least about 9%. It is also effective when it increases skin moisture on the canthus by from about 1% to about 90%, preferably by at least about 21%. It is effective when it increases skin moisture on the cheek by from about 1% to about 90%, preferably by at least about 14%.

The cosmetic composition should be topically applied regularly to whatever skin area requires treatment with the frequency and in the amount necessary to achieve the desired results. Preferably, the cosmetic composition is applied at least once per day, most preferably twice per day. The frequency of treatment depends on the degree of damage or deterioration of the skin, the responsiveness of the user's skin, the strength of the active ingredients in the cosmetic product, the effectiveness of the vehicle used to deliver the active ingredients into the stratum corneum, the ease with which the formula is removed by physical contact with clothing or it's removal by sweat or other intrinsic or extrinsic fluids, and the convenience to the user's lifestyle. Typical concentrations of relatively simple biochemically active substances such as the novel treatment composition described herein can range from about 0.01% to about 5.0% by weight based on the total weight of the cosmetic composition, and the formula should be applied to the skin at a rate equal to from about 1.0 mg/cm$^2$ of skin to about 20.0 mg/cm$^2$ of skin. Preferably, the formula should contain from about 0.39% to about 0.78% by weight based on the total weight of the cosmetic composition. Most preferably, the formula should contain about 0.78% active ingredients and be applied to the skin at a rate of about 5.0 mg/cm$^2$ of skin.

The cosmetic composition of the present invention comprises safe and effective amounts of one or more surfactants and at least one chelating agent. Use of these combinations of materials will result in an activation of one or more of the resident stratum corneum protease chymotryptic enzymes, which causes a loss of adherence between corneocytes, thus allowing them to be shed at a faster rate. While the mechanism or mechanisms of this activation process are unknown, we speculate that the surfactants could cause one or more of the following changes, including conformational changes in the enzyme, uncovering of the active site of the enzyme, or removal of lipids or other adherent substances from the enzyme. The chelating agent could somehow regulate the concentration of a metal cation which may be required for activity such as $Ca^{++}$, $Mg^{++}$, $Sr^{++}$, or $Mn^{++}$. The surfactants can be selected from any natural or synthetic surfactants suitable for use in cosmetic compositions and can be cationic, anionic, zwitterionic, non-ionic, or mixtures thereof. (See Rosen, M., "Surfactants and Interfacial Phenomena," Second Edition, John Wiley & Sons, New York, 1988, Chapter 1, pages 4-31). Suitable cationic surfactants can include, but are not limited to DMDAO or other amine oxides, long-chain primary amines, diamines and polyamines and their salts, quaternary ammonium salts, polyoxyethylenated long-chain amines, and quaternized polyoxyethylenated long-chain amines. Suitable anionic surfactants can include, but are not limited to SDS, salts of carboxylic acids (i.e. soaps), salts of sulfonic acids, salts of sulfuric acid, phosphoric and polyphosphoric acid esters, alkylphosphates, monoalkyl phosphate (MAP), and salts of perfluorocarboxylic acids.

Suitable zwitterionic surfactants can include but are not limited to cocoamidopropyl hydroxysultaine (CAPHS) and others which are pH-sensitive and require special care in designing the appropriate pH of the formula (i.e. alkylaminopropionic acids, imidazoline carboxylates, and betaines) or those which are not pH-sensitive (i.e. sulfobetaines, sultaines). Suitable non-ionic surfactants can include but are not limited to alkylphenol ethoxylates, alcohol ethoxylates, polyoxyethylenated polyoxypropylene glycols, polyoxyethylenated mercaptans, long-chain carboxylic acid esters, alkonolamides, tertiary acetylenic glycols, polyoxyethylenated silicones, N-alkylpyrrolidones, and alkylpolyglycosidases. Any combination of surfactants is acceptable. Preferably, the surfactant includes at least one anionic and one cationic surfactant, or at least one cationic and one zwitterionic surfactant which are compatible, e.g., do not form complexes which precipitate appreciably when mixed. Most preferably, the surfactant includes DMDAO and SDS, or DMDAO and MAP. Applicants believe that SDS and MAP are interchangeable in the present invention.

The chelating agent can be any chelating agent suitable for use in a cosmetic composition. Suitable chelating agents can include, but are not limited to any natural or synthetic chemical which has the ability to bind divalent cationic metals such as $Ca^{++}$, $Mn^{++}$, or $Mg^{++}$. Preferably, the chelating agent is selected from EDTA, disodium EDTA, EGTA, citric acid, or dicarboxylic acids. Most preferably, the chelating agent is EDTA.

Where the cosmetic composition contains a cationic surfactant such as DMDAO, the percent of such surfactant in the composition is from about 0.01% to about 5.0% by weight based on the total weight of the cosmetic composition, preferably from about 0.18% to about 0.36% and most preferably about 0.36%. Where the cosmetic composition contains an anionic surfactant such as SDS or MAP, the percent of such surfactant in the composition is from about 0.01% to about 5.0% by weight based on the total weight of the cosmetic composition, preferably from about 0.06% to about 0.12% and most preferably about 0.12%. The cosmetic composition includes a chelating agent such as EDTA at from about 0.01% to about 5.0% by weight based on the total weight of the cosmetic composition, preferably from about 0.15% to about 0.30% and most preferably about 0.30%.

While various combinations of surfactant and chelating agents may be used, the cosmetic composition of the present invention most preferably includes a combination of DMDAO/SDS/EDTA, alternatively the same concentration of MAP can substitute for the SDS. In the context of the present invention, a preferred composition is 0.18% DMDAO, 0.06% SDS and 0.15% EDTA by weight based on the total weight of the cosmetic composition. This composition has been designated as a IX concentration of the active ingredients. Concentration levels for this combination can range from between about 0.1× to about 10×, preferably from about 1× to about 3× and most preferably about 2×. The present invention provides aged or environmentally-damaged skin with anti-aging benefits which are comparable to those achieved with hydroxy acids and retinoids. Furthermore, the indicated combinations of DMDAO/SDS/EDTA are non-toxic, and non-irritating. In this context, "non-toxic" means that these materials, at the recommended concentrations and usage rates, do not damage living skin cells and "non-irritating" means that there are no periods of time during their use when these materials cause classical clinical irritation characterized by immunological reactions and/or burning, itching, stinging, erythema, or scaling of the skin. In marked contrast, efficacious levels of retinoids and hydroxy acids can cause the skin to experience all of these symptoms of irritation during the initial stages of treatment, and can persist indefinitely.

The indicated combinations of DMDAO/SDS/EDTA are effective in all suitable cosmetic vehicles, including emulsions, creams, lotions, solutions (both aqueous and hydro-alcoholic), anhydrous bases (such as lipsticks and powders), gels, and ointments. One skilled in the art would generally recognize these and other standard cosmetic vehicles that can be used in the present invention. Thus, the present invention may be formulated with a variety of cosmetic vehicles in addition to those described in the Examples below. Variations and other appropriate vehicles will be apparent to the skilled artisan and are appropriate for use in the present invention. Preferably, the cosmetic vehicle is selected from oil-in-water emulsions, hydro-alcoholic solutions, and encapsulated beads in anhydrous systems. Most preferably, the vehicle is an oil-in-water emulsion. Such emulsions and their compositions and methods of making are well known in the art. It is important, however, that the concentrations and combinations of the surfactants and chelating agents be selected in such a way that the combinations are chemically compatible and do not form complexes which precipitate from the finished product.

The composition of the present invention can be used in many cosmetic products including, but not limited to, moisturizing cream, skin benefit creams and lotions, gels, ointments, foundation, night cream, lipstick, cleansers, toners, masks, and color cosmetic products. The composition is most preferably used in anti-aging products for the face and other body parts, most especially leave-on products.

Products according to the present invention in which humectant properties are desired may include amino acids, chondroitin sulfate, diglycerin, erythritol, fructose, glucose, glycerin, glycerol, glycol, 1,2,6-hexanetriol, honey, hyaluronic acid, hydrogenated honey, hydrogenated starch hydrolysate, inositol, lactitol, maltitol, maltose, mannitol, natural moisturization factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Products according to the present invention in which anti-oxidant properties are desired may include acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

Products according to the present invention in which moisturizing properties are desired may include acetylated lanolin, acetylated lanolin alcohol, acrylates/C10-30 alkyl acrylate crosspolymer, acrylates copolymer, alanine, algae extract, aloe barbadensis, aloe barbadensis extract, aloe barbadensis gel, althea officinalis extract, aluminum starch octenylsuccinate, aluminum stearate, apricot (*prunus armeniaca*) kernel oil, arginine, arginine aspartate, arnica montana extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*oenothera biennis*) oil, fatty acids, tructose, gelatin, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated cocoglycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, macadamia ternifolia nut oil, magnesium stearate, magnesium sulfate, maltitol, matricaria (*chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquarternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (salvia officinalis) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium DNA, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

Products according to the present invention in which ultraviolet light (UVA and UVB) absorbing properties are desired may include benzophenone, benzophenone-1, benzophenone-2, benzophenone-3, benzophenone-4, benzophenone-5, benzophenone-6, benzophenone-7, benzophenone-8, benzophenone-9, benzophenone-10, benzophenone-11, benzophenone-12, benzyl salicylate, butyl PABA, cinnamate esters, cinoxate, DEA-methoxycinnamate, diisopropyl methyl cinnamate, ethyl dihydroxypropyl PABA, ethyl diisopropylcin namate, ethyl methoxycinnamate, ethyl PABA, ethyl urocanate, glyceryl octanoate dimethoxycinnamate, glyceryl PABA, glycol salicylate, homosalate, isoamyl p-methoxycinnamate, PABA, PABA esters, Parsol 1789, and isopropylbenzyl salicylate.

Additional skin care preparation ingredients include skin lightening agents (e.g. kojic acid, hydroquinine, ascorbic acid and derivatives, retinoids, etc.), hydroxy acids (e.g. lactic acid, salicylic acid, etc.), emollients (e.g. esters, fatty acids, etc.), vitamins (i.e. A, C, E, K, etc.), trace metals (e.g. zinc, calcium, selenium, etc.), anti-irritants (e.g. steroids, non-steroidal anti-inflammatories, etc.), antimicrobial agents (e.g. triclosan, etc.), botanical extracts (e.g. aloe vera, chamomile, cucumber extract, ginkgo bibloba, ginseng, rosemary, etc.), dyes and color ingredients (e.g. D&C blue no. 4, D&C green is no. 5, D&C orange no. 4, D&C red no. 17, D&C red no. 33, D&C violet no. 2, D&C yellow no. 10, D&C yellow no. 11, DEA-cetyl phosphate), preservatives (e.g. BHA), emollients (i.e. organic esters, fatty acids, lanolin and its derivatives, plant and animal oils and fats, di- and triglycerides, etc.), antiirritants (i.e., steroids, nonsteroidal antiinflammatories, glycyrrhizates, etc.), antimicrobial agents (i.e., triclosan, ethanol, etc.), and fragrances (natural and artificial).

One skilled in the art will understand that the terms "mixture" and "mixing" in this patent are used in the broad sense of the words, with the term "mixing" including, but not limited to, stirring, blending, dispersing, milling, homogenizing, and other similar methods.

The cosmetic composition of the present invention is effective at pH values between about 2.5 and about 10.0. Preferably, the pH of the composition is between the following pH ranges: about 5.5 and about 8.5, about 5 to about 10, about 5 to about 9, about 5 to about 8, about 3 to about 10, about 3 to about 9, about 3 to about 8, and about 3 to about 8.5. Most preferably, the pH is about 8. One of ordinary skill in the art may add appropriate pH adjusting ingredients to the compositions of the present invention to adjust the pH to an acceptable range.

EXAMPLES

Three main types of experiments were performed to screen the potential for formulas to provide anti-aging benefits to skin. These were (1) stratum corneum transit time, as measured by the rate of loss of skin color following treatment with dihydroxy acetone, (2) barrier integrity, as measured by temporary trans-epidermal water loss (TEWL) following overnight treatment with occlusive patches containing the test material, and (3) tests for actual facial skin benefit, including measurements of skin moisture on the face, long term TEWL, skin firmness, number of wrinkles around the canthus (the corner of the eye), texture (roughness) of the canthus skin, skin scales, and expert grading evaluations.

Stratum Corneum Turnover Studies

Example 1

The following procedure was used to estimate corneum transit time. As many as different sites per forearm were marked using a plastic template, and baseline readings of color intensity were determined using a Minolta chromameter (b* value). Occlusive Hilltop chambers (2 cm diameter) containing 0.02 ml Mary Kay Sun Essentials® Sunless Tanning Lotion product with dihydroxy acetone ("DHA") were placed on the sites. After 6 hours, these patches were removed, and 18 hours later, the color intensity was again determined using the chromameter; the delta b (Δb) values were calculated as the difference between the reading and the baseline. Panelists themselves applied the products to the brown spots in the morning and evening during the ensuing 10 days, and chromameter readings were repeated after 3, 5, 7, and 10 days. The color decay slope was calculated as the percent loss per day, and the transit time determined by extrapolating to 100% loss of color.

The activity of the DSE is not dependent on the vehicle, as long as the vehicle is a suitable carrier of the DSE components to the surface of the skin. For the experiments to be described, five different vehicles were used, which are referred to as vehicles A, B, C, D, and E. Vehicle A is a simple non-moisturizing, non-drying oil-in-water emulsion (75% water) which is routinely used to dissolve hydrophobic or hydrophilic ingredients for testing on the skin. Vehicle B is a proprietary, oil-in-water emulsion (62% water) which contains UVA and UVB sunscreens (SPF 15). Vehicle C is a proprietary non-ionic, highly-moisturizing oil-in-water emulsion (61% water). Vehicle D is a proprietary, anhydrous formula which contains DSE incorporated into porous Nylon 12 particles (final formula <5% water). Vehicle E is a proprietary, highly-moisturizing oil-in-water emulsion (57% water).

Table 1 shows the effects of 0.18% DMDAO+0.06% SDS+ 0.15% EDTA on human stratum corneum turnover rates (i.e. transit time), as determined by the DHA disappearance on forearm skin. Vehicle A is a control, oil-in-water, non-drying, non-moisturizing emulsion developed as a vehicle to test for the effects of materials on skin.

As shown in Table 1, whereas the transit time was 13.0 days for Vehicle A alone, addition of 0.18% DMDAO+0.06% SDS+0.15% EDTA reduced the transit time to 7.8 days, which represents a 40.0% reduction (p=0.030). The number of panelists=11. The difference between the two treatments, as determined by paired Student t tests, was statistically significant at the 97% confidence level.

While U.S. Pat. No. 5,720,963 teaches that the use of a surfactant, such as sodium lauryl sulfate, alone can provide benefit to aged skin, the mechanism by which the benefit occurs is totally different in the present invention. The benefit in U.S. Pat. No. 5,720,963 depends on chronic disruption of the stratum corneum barrier, which is an unnatural event; caused by the partial removal and/or disruption of the special molecular packing of the intercorneocyte lipids by surfactants. This causes injury and damage to the skin. That patent also teaches that chronic barrier disruption can be achieved by the insertion of "abnormal" cerebrosides into the lipid lamellae structures, or by the creation of a thick, scaly layer or stratum corneum by stimulating rapid division of epidermal basal cells with Vitamin A palmitate.

In contrast, the mechanism of the present invention involves activation of the natural mechanism for desquamation (i.e., activation of a protease enzyme), which results in stimulation of epidermal cell renewal. The combination of ingredients in the composition of the present invention does not cause damage to the skin because the concentrations that are used are lower than the critical micelle concentration of the surfactants.

As seen with other agents such as retinoids and hydroxy acids, it can be expected that a reduction in corneum transit time will provide skin with anti-aging benefits. The term "anti-aging benefits" as used herein means any reversal of the physical or functional changes which occur in skin as a result of intrinsic (i.e. natural) aging as caused by the passage of time, or environmentally-induced changes due to sun, weather conditions, or exposure to adverse chemical substances. Examples of benefits include, but are not limited to improvements in the following: fine lines and wrinkles, uneven pigmentation, excessive dryness, excessive roughness, fragility, corneum water holding capacity, microcirculation, elasticity, firmness, epidermal turnover rates, and dermal water content.

TABLE 1

| Treatment | Corneum Turnover Time (Days) | % Reduction in Turnover Time |
| --- | --- | --- |
| Vehicle A | 13.0 | — |
| Vehicle A + DMDAO/SDS/EDTA | 7.8 | 40.0 |

Example 2

The same procedure as in Example 1 was followed for preparing sites, applying products and evaluating transit time. Table 2 shows the effects of once per day vs twice per day application of 0.18% DMDAO+0.06% SDS+0.15% EDTA in Vehicle B on human stratum corneum turnover rates, as determined by DHA disappearance on forearm skin. Vehicle B is a sunscreen formula.

Once per day application of the formula (e.g., in the morning) reduced the transit time by 24.8% compared to the untreated control sites (p=0.045), and twice per day application of the formula (e.g., morning and evening) reduced the transit time 34.9% (p=0.005). Thus, twice-a-day application of a topical product containing the inventive composition will provide more anti-aging benefit than if the product is used only once per day. Number of panelists=10.

TABLE 2

| Treatment | Corneum Turnover Time (Days) | % Reduction in Turnover Time |
| --- | --- | --- |
| No Treatment | 10.9 | — |
| Vehicle B + DMDAO/SDS/EDTA Morning Application Only | 8.2 | 24.8 |
| Vehicle B + DMDAO/SDS/EDTA Morning and Evening Application | 7.1 | 34.9 |

Example 3

The same procedure as in Example 1 was followed for preparing sites, applying products and evaluating transit time. Experiments were performed to assess the effects of DMDAO/SDS/EDTA concentration and pH on corneum turnover rates as determined by the DHA disappearance on forearm skin. The indicated materials were formulated into Vehicle A. A 1× concentration=0.18% DMDAO, 0.06% SDS, and 0.15% EDTA, at the indicated pH; a 2× concentration is double these concentrations. Number of panelists=10. The results as shown in Table 3 clearly demonstrate that there does exist a DMDAO/SDS/EDTA concentration-dependence, with the higher concentration giving higher increases in turnover rates at all pH values. Furthermore, the increased pH gave higher values. Thus, as expected for an enzyme-mediated effect, the effects were concentration- and pH-dependent.

TABLE 3

| Treatment | Corneum Turnover Time (Days) | % Reduction in Turnover Time |
|---|---|---|
| No Treatment | 18.9 | — |
| 1× DMDAO/SDS/EDTA, pH 5 | 15.0 | 20.6 |
| 2× DMDAO/SDS/EDTA, pH 5 | 14.0 | 25.9 |
| 1× DMDAO/SDS/EDTA, pH 6.5 | 14.9 | 21.2 |
| 2× DMDAO/SDS/EDTA, pH 6.5 | 14.8 | 21.7 |
| 1× DMDAO/SDS/EDTA, pH 8.0 | 13.1 | 30.7 |
| 2× DMDAO/SDS/EDTA, pH 8.0 | 12.3 | 34.9 |

Example 4

The same procedure as in Example 1 was followed for preparing sites, applying products, and evaluating stratum corneum transit time. This experiment was performed to assess the effects of DMDAO/SDS/EDTA when formulated into Vehicle D, a proprietary anhydrous formula in which the DSE was incorporated into porous Nylon 12 particles, which were then added to the formula. The concentration of DSE in this formula was 2×, and the product was applied twice per day. Number of panelists=12.

TABLE 4

| Treatment | Corneum Turnover Time (Days) | % Reduction in Turnover Time |
|---|---|---|
| No Treatment | 14.8 | — |
| Vehicle D | 14.0 | 5.4 |
| Vehicle D + 2× DMDAO/SDS/EDTA | 10.8 | 27.4 |

As shown in Table 4, whereas the transit time was 14.8 days for the untreated sites, Vehicle D alone did not reduce the transit time to a statistically significant level. Addition of 2×DMDAO/SDS/EDTA to Vehicle D reduced the transit time to 10.8 days, which represents a 27.4% reduction.

Example 5

The same procedure as in Example 1 was followed for preparing sites, applying products, and evaluating stratum corneum transit time. This experiment was performed to assess the effects of substituting a different surfactant for SDS in the DMDAO/SDS/EDTA. The vehicle for this experiment was Vehicle E, which is a proprietary, highly-moisturizing oil-in-water emulsion. Four different formulas were prepared, all using Vehicle E as the base. While DMDAO and EDTA were included at 1× concentrations in all four formulas, the SDS was substituted with equimolar concentrations of either an amphoteric surfactant (cocoamidopropyl hydroxysultaine), or an anionic surfactant ($C_9$-$C_{15}$ monoalkyl phosphate). The products were applied twice per day, and the number of panelists=20.

TABLE 5

| Treatment | Corneum Turnover Time (Days) | % Reduction in Turnover Time |
|---|---|---|
| No Treatment | 19.3 | — |
| Vehicle E + DMDAO + sodium dodecyl sulfate + EDTA | 17.2 | 10.5 |
| Vehicle E + DMDAO + cocoamphodiacetate + EDTA | 19.9 | −3.3 |
| Vehicle E + DMDAO + decyl polyglucose + EDTA | 18.4 | 4.3 |
| Vehicle E + DMDAO + cocoamidopropyl hydroxysultaine + EDTA | 17.8 | 7.3 |
| Vehicle E + DMDAO + monoalkyl phosphate + EDTA | 17.5 | 9.0 |

As shown in Table 5, the combination of DMDAO+SDS+EDTA reduced the corneum transit time 10.5% (p vs no treatment=0.031). Substitution of the zwitterionic surfactant cocoamidopropyl hydroxysultaine for SDS similarly reduced transit time (7.3% reduction, p vs no treatment=0.045) as did the anionic surfactant monoalkyl phosphate (9.0% reduction, p vs no treatment=0.017). In contrast, the amphoteric surfactant cocoamphodiacetate did not reduce transit time (−3.3% reduction, p vs no treatment=0.348). Similarly, the non-ionic surfactant decyl polyglucose did not reduce transit time (4.3% reduction, p vs no treatment=0.451). There were no statistical differences between the formula containing SDS and cocoamidopropyl hydroxysultaine (p=0.209) or monoalkyl phosphate (MAP) (p=0.253). In conclusion, while an other anionic surfactant (MAP) and a zwitterionic surfactant (cocoamidopropyl hydroxysultaine, which has anionic character at the pH tested) substituted for SDS in this invention, the amphoteric or nonionic surfactants (cocoamphodiacetate and decyl polyglucose) that were tested did not substitute for the SDS.

Barrier Impact Study

Example 6

Corneum protease activation is believed to result in corneocyte dyshesion and an increase in the rate of stratum corneum turnover. Because water loss through the stratum corneum occurs by passage through the intercorneal lipid lamellar structures, trans-epidermal water loss ("TEWL") measurements were employed to screen for barrier "loosening". An experiment was performed to assess the acute (i.e., short term) effects of DMDAO/SDS/EDTA concentrations and formula pH on TEWL. Testing involved application of the formulas overnight under occlusive skin patches. The forearms of human subjects were patched overnight with the indicated formulas, the patches were removed, and TEWL was measured 6 hours later using a ServoMed evaporimeter. The data are presented as % increased TEWL compared to the pre-patch baseline values. The indicated materials were formulated into Vehicle A. A 1× concentration=0.18% DMDAO, 0.06% SDS, and 0.15. % EDTA, at the indicated pH; a 2× concentration is double these concentrations. Number of panelists=10.

The data, shown in Table 6, clearly demonstrate that when using this acute occlusive test protocol, there was a DSE concentration-dependence, with the higher concentration giving marginal increases in TEWL at all pH values.

TABLE 6

| Treatment | % Increased TEWL vs Baseline |
| --- | --- |
| Vehicle A, pH 5 | 9.9 |
| 1× DMDAO/SDS/EDTA, pH 5 | 14.7 |
| 2× DMDAO/SDS/EDTA, pH 5 | 15.1 |
| Vehicle A, pH 6.5 | 17.7 |
| 1× DMDAO/SDS/EDTA, pH 6.5 | 18.8 |
| 2× DMDAO/SDS/EDTA, pH 6.5 | 21.0 |
| Vehicle A, pH 8.0 | 7.3 |
| 1× DMDAO/SDS/EDTA, pH 8.0 | 22.7 |
| 2× DMDAO/SDS/EDTA, pH 8.0 | 23.7 |

Chronic Efficacy Studies

Example 7

The effects of the combination of 0.18% DMDAO, 0.06% SDS, and 0.15% EDTA in Vehicle B were tested for actual facial skin benefit. After taking baseline measurements, panelists applied the product to their face twice per day for a 28-day period, after which the measurements were again taken. Skin moisture was determined using the Nova Dermal Phase Meter (impedance), TEWL using the ServoMed evaporimeter, firmness using the Cutometer 474 (R0 value), number of wrinkles on the canthus by image analysis of Silflo replicas, and canthus texture/roughness using image analysis of Silflo replicas (Ra value). The product was not applied on the morning for which the measurements were taken. Number of panelists=9. From Table 7 it can be clearly seen that this composition increased skin moisture on the face, improved the water barrier (i.e. reduced TEWL), increased firmness, improved the texture of the canthus skin, and reduced the number of wrinkles around the canthus. It is noteworthy that while the immediate effects of the DMDAO/SDS/EDTA combination, when applied in occlusive patches overnight, loosens the corneum and results in increased TEWL (Table 6), the long-term effects of topical application of the inventive formula to the skin results in the formation of a better-functioning, healthier corneum which provides a better barrier as measured by reduced water loss from the skin. This further supports the conclusion that the mechanisms by which the inventive DMDAO/SDS/EDTA combination operates differently from prior art mechanisms, which chronically increase TEWL. A chronic increase in TEWL represent chronic skin damage, which causes the skin to repair itself.

TABLE 7

| Skin Benefit | % Improvement from Baseline | p values vs Baseline |
| --- | --- | --- |
| Moisture (Canthus) | 21.6 | 0.001 |
| Moisture (Cheek) | 14.5 | 0.003 |
| TEWL (Cheek)(Reduced) | 10.8 | 0.028 |
| Firmness (Cheek), R0 | 11.1 | 0.103 |
| Roughness, Canthus, Ra | 9.9 | 0.012 |
| # Wrinkles, Canthus | 9.8 | 0.007 |

Another chronic study was performed to illustrate the beneficial effects on the face of a combination of 0.18% DMDAO, 0.06% SDS, and 0.15% disodium EDTA in Vehicle C. Vehicle C is a moisturizing formula.

After baseline measurements were taken, 13 human volunteers applied the product to their face twice per day (morning and evening). The product was not applied on the morning for which the measurements were taken. In addition to the measurements described for the experiment in Table 7, an expert graded the severity of the canthus fine lines and wrinkles (modified Packman scoring system) and D'Squames were taken on the cheek. The D'Squames test (Cuderm Corp., Dallas, Tex.) evaluates skin condition by applying tape to the skin and pulling it off (tape stripping). The quality and amount skin adhering to the tape is then determined by computer-aided image analysis. This technique is well known in the art of measuring skin condition. The D'Squames were evaluated for fine and coarse flakes. The resulting improvements in facial skin after a 28-day treatment period are shown in Table 8. The results clearly show statistically-significant improvements in terms of facial moisture, increased stratum corneum barrier integrity (i.e., reduced TEWL), increased elasticity, decreased wrinkles and fine lines, and decreased scales.

TABLE 8

| SKIN BENEFIT | % Improvement from Baseline | p value vs Baseline |
| --- | --- | --- |
| Moisture (Canthus) | 30.8 | 0.00 |
| Moisture (Cheek) | 26.7 | 0.00 |
| TEWL (Cheek) (Reduced) | 36.1 | 0.00 |
| Canthus Wrinkles (Expert Grading) | 39.6 | 0.00 |
| Canthus Wrinkles (Replicas) | 11.7 | 0.03 |
| D'Squames (Cheek Scales) | 77.2 | 0.02 |
| Elasticity (Cheek) | 13.4 | 0.01 |

Example 8

Longer term clinical benefits of the composition of the present invention have also been evaluated. Thirty panelists applied products (a combination cleanser/mask/toner and a moisturizer) to their skin as part of their regular morning and evening skincare routine. These products included a total 2.84× concentration of the active ingredients of the invention, with MAP substituted for SDS.

The panelists were monitored for skin improvement at the beginning of the study, and at 2, 4, 6, and 8 weeks. They were evaluated for face and neck moisture, dryness, surface fine lines, canthus wrinkles, firmness, smoothness, softness, clarity, neck texture, skin barrier, skin brightness, and evenness of tone.

Face and neck moisture were evaluated using impedance measurements, an electrical conductivity measurement using the Nova Dermal Phase Meter. Dryness, surface fine lines, smoothness, softness, skin brightness, and evenness of tone were determined by an expert grader using a calibrated visual analog scale from 1 to 10. Skin smoothness and softness were evaluated using tactile observations by the grader. Surface fine lines were both counted and the severity of the lines evaluated generally according to the Packman-Gans method, J. Soc. Cosmetic Chem. 29:70 (1978), using weighted scoring. Dryness, skin brightness, and evenness of tone were evaluated using a calibrated visual analog scale from 1 to 10.

Firmness was evaluated using a Hargens ballistometer, a device that evaluates the elasticity and firmness of the skin by dropping a small body onto the skin and recording its first two rebound peaks. As firmness and elasticity decrease the second peak will be smaller in comparison to the first. Clarity was evaluated using a Minolta Chromameter, which measures the total light reflected from the skin compared to the amount of red and brown/yellow light. These measurements are mathematically analyzed to determine the clarity of the skin.

Skin Barrier or TEWL (trans epidermal water loss) is measured using a Servo Madr Register Evaporimeter EP1, which uses a probe to measure water vapor as it leaves the skin. Canthus wrinkles and neck texture were evaluated by comparing the skin to silicone replicas (negative impressions) made of the individuals' skin at baseline. The post-treatment silicone replicas were evaluated by computer image analysis to determine the number and depth of the wrinkles compared to pretreatment replicas.

As shown in Table 9, continued improvement was seen for the vast majority of skin condition parameters throughout the 8 weeks of the study. The small increase in skin barrier was not statistically significant.

TABLE 9

| Benefit | % Improvement from Baseline | | | |
|---|---|---|---|---|
| | 2 Weeks | 4 Weeks | 6 Weeks | 8 Weeks |
| Face Moisture | 18.1 | 27.1 | 30.8 | 39.9 |
| Neck Moisture | 14.2 | 30.1 | 36.2 | 43.3 |
| Dryness | 28.1 | 33.7 | 39.2 | 50.8 |
| Surface Fine Lines | 17.5 | 20.8 | 28.6 | 34.7 |
| Canthus Wrinkles | 11.7 | 22.3 | 29.5 | 36.5 |
| Firmness | 10.7 | 17.3 | 18.3 | 24.6 |
| Smoothness | 26.4 | 38.6 | 50.7 | 64.1 |
| Softness | 30.4 | 63.2 | 82.0 | 98.6 |
| Clarity | 3.8 | 6.7 | 7.2 | 7.9 |
| Neck Texture | 3.7 | 8.6 | 14.7 | 28.3 |
| Skin Barrier | 0.8 | 3.1 | 3.9 | 4.2 |
| Skin Brightness | 5.7 | 12.6 | 20.3 | 26.1 |
| Evenness of Tone | 6.1 | 16.1 | 18.0 | 26.1 |

While illustrative embodiments of the invention have been described above and are attached, it is, of course, understood that various modifications will be apparent to those of ordinary skill in the art.

What is claimed is:

1. A topical skin composition comprising:
   (i) a chemically compatible combination of one or more surfactants and at least one chelating agent;
   (ii) magnesium ascorbyl phosphate;
   (iii) *citrus medica limonum* oil; and
   (iv) cucumber extract,
   wherein the compositing is formulated for topical application to skin.

2. The composition of claim 1, wherein the composition is an emulsion.

3. The composition of claim 1, wherein the composition is a cream, a lotion, a gel, or an ointment.

4. The composition of claim 1, wherein the composition is a solution.

5. The composition of claim 1, wherein the composition is an anhydrous base.

6. The composition of claim 1 wherein the composition comprises a cationic surfactant and an anionic surfactant.

7. The composition of claim 6, wherein the cationic surfactant is N,N,-dimethyldodecyl amine oxide.

8. The composition of claim 6, wherein the anionic surfactant is sodium dodecyl sulfate or monoalkyl phosphate.

9. The composition of claim 6, wherein the chelating agent is ethylene diamine tetraacetate.

10. The composition of claim 1, wherein the composition is a skin lightening composition.

11. A method of treating skin comprising topically applying the composition of claim 1 to the skin.

12. The method of claim 11, wherein the composition is an emulsion.

13. The method of claim 11, wherein the composition is a cream, a lotion, a gel, or an ointment.

14. The method of claim 11, wherein the composition is a solution.

15. The method of claim 11, wherein the composition is an anhydrous base.

16. The method of claim 11, wherein the composition further comprises a surfactant and a chelating agent.

17. The method of claim 16, wherein the composition comprises a cationic surfactant and an anionic surfactant.

18. The method of claim 17, wherein the cationic surfactant is N,N,-dimethyldodecyl amine oxide.

19. The method of claim 17, wherein the anionic surfactant is sodium dodecyl sulfate or monoalkyl phosphate.

20. The method of claim 17, wherein the chelating agent is ethylene diamine tetraacetate.

21. The method of claim 11, wherein the composition lightens the skin.

* * * * *